United States Patent
Kunimura

(10) Patent No.: US 11,630,093 B2
(45) Date of Patent: Apr. 18, 2023

(54) ANALYTICAL DATA ANALYSIS SYSTEM

(71) Applicant: SHIMADZU CORPORATION, Kyoto (JP)

(72) Inventor: Yoshihiro Kunimura, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 637 days.

(21) Appl. No.: 16/774,093

(22) Filed: Jan. 28, 2020

(65) Prior Publication Data

US 2020/0340961 A1 Oct. 29, 2020

(30) Foreign Application Priority Data

Apr. 24, 2019 (JP) .............................. JP2019-082555

(51) Int. Cl.
*G01N 30/86* (2006.01)
*G01N 33/28* (2006.01)
*G01N 30/02* (2006.01)

(52) U.S. Cl.
CPC ..... *G01N 30/8679* (2013.01); *G01N 30/8637* (2013.01); *G01N 33/2835* (2013.01); *G01N 2030/025* (2013.01)

(58) Field of Classification Search
None
See application file for complete search history.

(56) References Cited

U.S. PATENT DOCUMENTS

| | | | | |
|---|---|---|---|---|
| 2004/0143461 A1* | 7/2004 | Watkins | .................. | G16H 10/60 600/300 |
| 2009/0179147 A1* | 7/2009 | Milgram | ............ | G01N 30/8675 250/281 |
| 2016/0091467 A1* | 3/2016 | Morris | ............... | G01N 30/7206 73/23.37 |
| 2019/0043703 A1* | 2/2019 | Bern | .................. | G01N 33/6848 |

FOREIGN PATENT DOCUMENTS

JP 2007-114041 A 5/2007

* cited by examiner

*Primary Examiner* — Catherine T. Rastovski
(74) *Attorney, Agent, or Firm* — Sughrue Mion, PLLC

(57) ABSTRACT

An analytical data analysis system (2) is a system that identifies composition substances contained in the sample to be analyzed and non-composition substances that are not the composition substance contained in the sample to be analyzed by comparing a standard chromatogram and an analysis target chromatogram. The analytical data analysis system (2) includes a non-composition substance information holding part (12) holding identification information and information on a peak expression position on a chromatogram of substances that may exist as the non-composition substance, a chromatogram synthesis part (16) configured to synthesize the information held in the non-composition substance information holding part with the standard chromatogram in order to describe identification information and the peak expression position of the substances that may exist as the non-composition substance on the standard chromatogram in which the composition substances of the standard sample are described, and a chromatogram display part (18) con- (Continued)

figured to display the analysis target chromatogram together with the standard chromatogram synthesized by the chromatogram synthesis part (16) on the display device (6).

4 Claims, 2 Drawing Sheets

ANALYTICAL DATA ANALYSIS SYSTEM

BACKGROUND OF THE INVENTION

1. Field of the Invention

The present invention relates to an analytical data analysis system for identifying peak components expressed in a chromatogram acquired by a chromatograph, such as a gas chromatograph.

2. Description of the Related Art

In composition substances of gasoline, there exist a large number of substances classified into components, such as paraffin (P), olefin (O), naphthene (N), and aromatic (A), depending on the number and structure of carbon. As a gasoline analysis technique, PONA analysis is often used in which substances contained in gasoline are classified into components of P, O, N, and A, and an amount of each component is quantified. In PONA analysis, analytical data of gasoline to be analyzed (sample to be analyzed) is compared with analytical data of gasoline as a reference (standard sample), so that what substance is a peak expressed in a chromatogram of the sample to be analyzed is identified (See Japanese Patent Laid-open Publication No. 2007-114041).

SUMMARY OF THE INVENTION

Since there are a large number of gasoline composition substances, and peaks of a plurality of substances are close to each other on a chromatogram, the identification work is extremely complicated. Furthermore, a sample to be analyzed often contains a non-composition substance that is different from a composition substance of a standard sample. In such a case, a peak that does not exist in a chromatogram of the standard sample is expressed in the chromatogram of the sample to be analyzed. By such a peak, a substance cannot be identified by comparison with a chromatogram of the standard sample, and the identification work of the substance contained in the sample to be analyzed has been further complicated and difficult.

The present invention has been made in view of the above problems, and an object of the present invention is to improve the efficiency of identification work of a composition substance and a non-composition substance contained in a sample to be analyzed.

An analytical data analysis system according to the present invention identifies composition substances contained in the sample to be analyzed and non-composition substances that are not the composition substance contained in the sample to be analyzed by comparing a standard chromatogram and an analysis target chromatogram. The standard chromatogram is a chromatogram created based on analytical data acquired by a chromatograph for a standard sample of a sample composed of specific composition substances. The analysis target chromatogram is a chromatogram created based on analytical data acquired by a chromatograph for a sample to be analyzed. The analytical data analysis system includes a display device for displaying information, a non-composition substance information holding part holding identification information and information on a peak expression position on a chromatogram of substances that may exist as the non-composition substance, a chromatogram synthesis part configured to synthesize the information held in the non-composition substance information holding part with the standard chromatogram in order to describe identification information and the peak expression position of the substances that may exist as the non-composition substance on the standard chromatogram in which the composition substances of the standard sample are described, and a chromatogram display part configured to display the analysis target chromatogram together with the standard chromatogram synthesized by the chromatogram synthesis part on the display device.

In the analytical data analysis system according to the present invention, information of the non-composition substances is synthesized with the standard chromatogram, the identification information and peak expression positions of the substances that may exist as the non-composition substance are described on the standard chromatogram on which the composition substances of the standard sample are described, and the synthesized standard chromatogram is displayed on the display device together with the chromatogram of the sample to be analyzed. Accordingly, even in a case where a non-composition substance different from the composition substance of the standard sample is contained in the sample to be analyzed, the identification work of the substances can be easily performed.

DETAILED DESCRIPTION OF THE INVENTION

Figure 1:
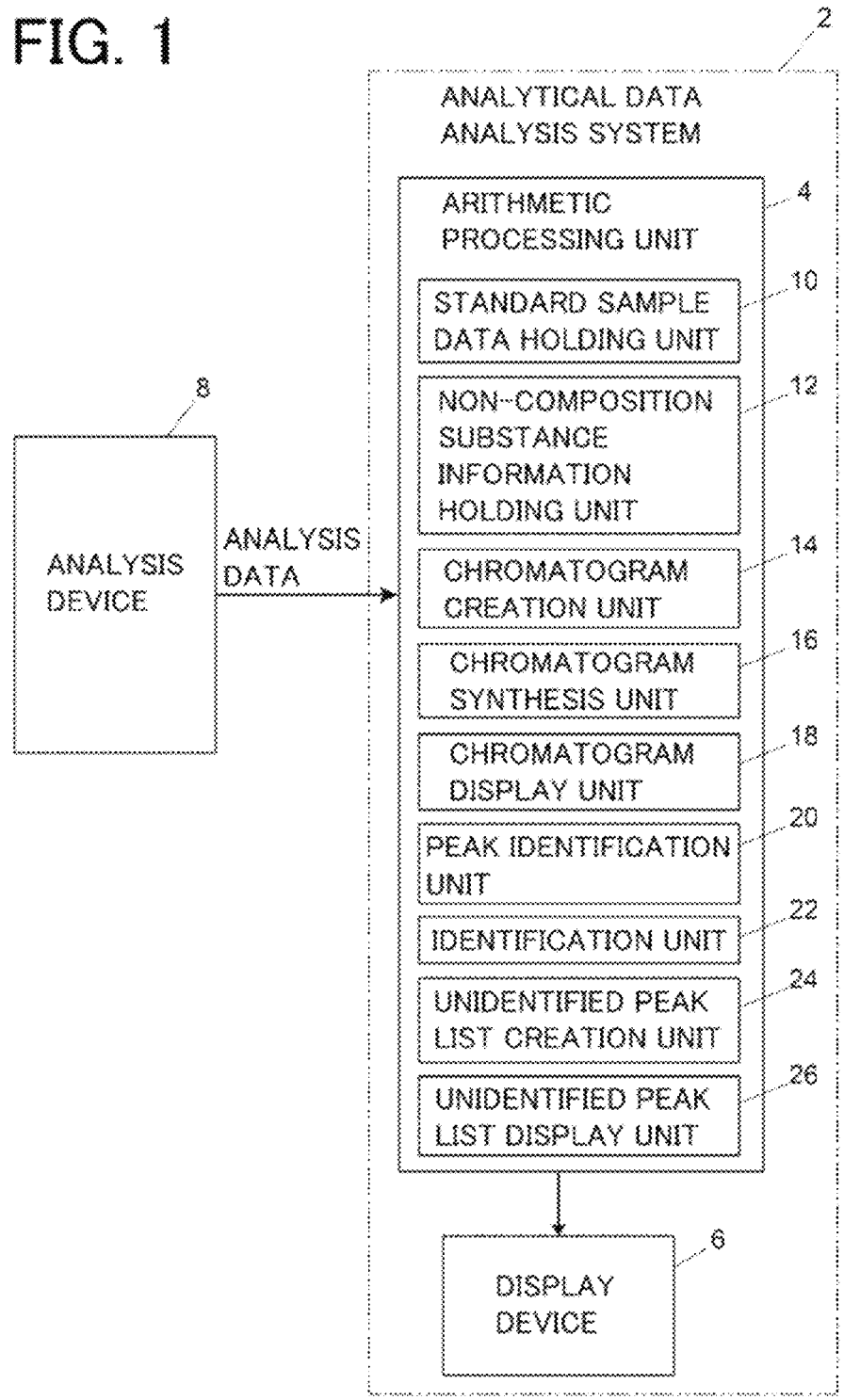
FIG. 1 is a schematic configuration diagram showing an embodiment of an analytical data analysis system.

Hereinafter, an embodiment of an analytical data analysis system of the present invention will be described with reference to the drawings.

An analytical data analysis system 2 of the present embodiment includes an arithmetic processing part 4 and a display device 6. The arithmetic processing part 4 has a function of taking in analytical data acquired by an analysis device 8 such as a gas chromatograph and analyzing the analytical data. The arithmetic processing part 4 can be realized by a computer circuit including a central processing part (CPU) and a storage device. The display device 6 is electrically connected to the arithmetic processing part 4 or realized by a liquid crystal display or the like provided on the arithmetic processing part 4.

The arithmetic processing part 4 includes a standard sample data holding part 10, a non-composition substance information holding part 12, a chromatogram creation part 14, a chromatogram synthesis part 16, a chromatogram display part 18, a peak identification part 20, an identification part 22, an unidentified peak list creation part 24, and an unidentified peak list display part 26. The standard sample data holding part 10 and the non-composition substance information holding part 12 are functions realized by a partial storage area of a storage device provided in the arithmetic processing part 4. The chromatogram creation part 14, the chromatogram synthesis part 16, the chromatogram display part 18, the peak identification part 20, the identification part 22, the unidentified peak list creation part 24, and the unidentified peak list display part 26 are functions realized by a program executed by a CPU in the arithmetic processing part 4.

The standard sample data holding part 10 holds analytical data for a standard sample of a sample (for example, regular gasoline, premium gasoline) composed of specific composition substances. The analytical data held in the standard sample data holding part 10 includes information necessary for creating a chromatogram, such as identification information (for example, a substance name) of composition substances of a sample, retention time in chromatographic analysis, a bandwidth, and the like.

The non-composition substance information holding part 12 holds information on non-composition substances that are not composition substances of a sample. The information held in the non-composition substance information holding part 12 includes information necessary for creating a chromatogram, such as identification information (for example, a substance name) of non-composition substances, retention time in chromatographic analysis, a bandwidth, and the like. The "non-composition substances" are substances that are not composition substances of a sample but may be mixed into the sample for some reason. The standard sample is a sample that is substantially free (or contains a negligibly small amount) of such non-composition substances.

The chromatogram creation part 14 is configured to create a chromatogram of the sample to be analyzed (analysis target chromatogram) based on the analytical data of the sample to be analyzed taken in from the analysis device 8, and create a chromatogram for standard use (standard chromatogram) based on the analytical data of the standard sample held in the standard sample data holding part 10.

The chromatogram synthesis part 16 is configured to synthesize the information on the non-composition substances held in the non-composition substance information holding part 12 with the standard chromatogram in order to display peak expression positions of the non-composition substances together with its identification information on the standard chromatogram created by the chromatogram creation part 14. In the synthesized standard chromatogram, each piece of identification information (for example, a substance name) is described at a peak position of the composition substance of the sample, and each piece of identification information (for example, a substance name) is displayed at a peak expression position of the non-composition substance in a mode visually distinguished from the composition substance.

In the present embodiment, the chromatogram synthesis part 16 is further configured to synthesize information on a non-composition substance held in the non-composition substance information holding part 12 with the analysis target chromatogram in order to display peak expression positions of the non-composition substances together with its identification information on the analysis target chromatogram created by the chromatogram creation part 14. In the synthesized analysis target chromatogram, identification information (for example, a substance name) is described at the peak expression positions of the non-composition substances.

Figure 2:
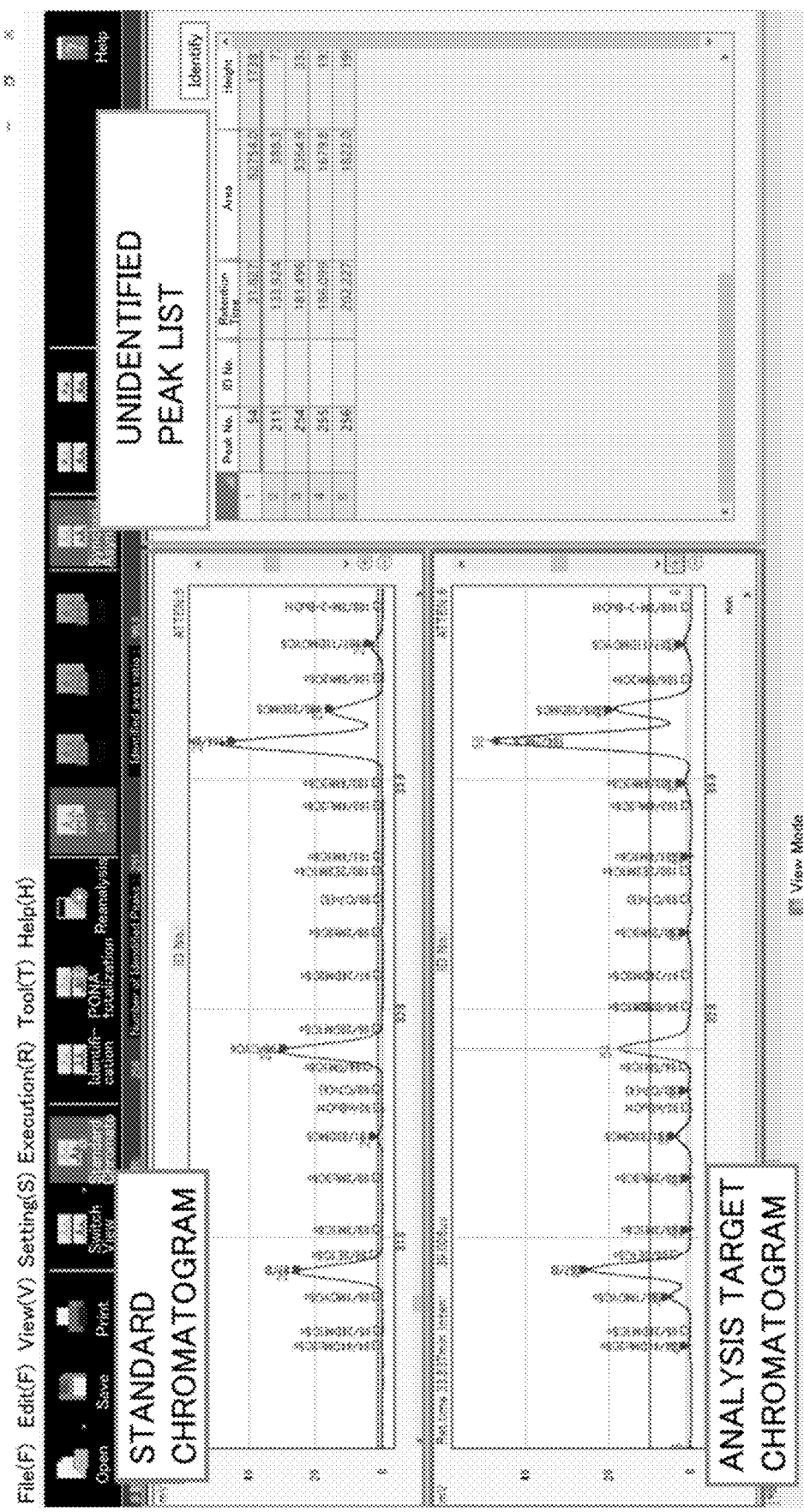
FIG. 2 is an example of a displayed screen according to the embodiment.

The chromatogram display part 18 is configured to display the standard chromatogram synthesized by the chromatogram synthesis part together with the analysis target chromatogram created by the chromatogram creation part 14 on the display device 6 according to an instruction from the user. As shown in FIG. 2, the standard chromatogram synthesized with the analysis target chromatogram is displayed on the display device 6 in a manner that the standard chromatogram and the analysis target chromatogram are arranged side by side in a state where time axes of the chromatograms are aligned, so that which of the composition substances and the non-composition substances described on the synthesized standard chromatogram corresponds to the peak expressed on the analysis target chromatogram can be identified by visual comparison. In the standard chromatogram shown in FIG. 2, mark indicating the peak expression positions of the composition substances are black, and marks indicating the peak expression positions of the non-composition substances are white.

The peak identification part 20 is configured to recognize peaks expressed in the analysis target chromatogram created by the chromatogram creation part 14 and identify individual peaks. The peaks can be recognized by detecting start points and end points of the peaks. A start point and an end point of a peak can be detected by comparing a slope of a chromatogram with a predetermined threshold value. Identification of a peak can be performed by, for example, sequentially assigning numbers to peaks of substances that are quickly eluted from a separation column.

The identification part 22 is configured to identify a substance corresponding to each of the peaks identified by the peak identification part 20 using the standard chromatogram synthesized by the chromatogram synthesis part 16. The identification can be performed manually or automatically. The manual identification can be performed by the user designating a substance described on the standard chromatogram for any peak on the analysis target chromatogram. The automatic identification can be performed in a manner that, for example, retention time and a bandwidth of a peak are compared with those of a composition substance or a non-composition substance described on the standard chromatogram, and whether or not a difference in the retention time and the bandwidth is within a predetermined allowable range is determined.

The unidentified peak list creation part 24 is configured to create a list (unidentified peak list) of unidentified peaks that have not been identified by the identification part 22 among peaks of the analysis target chromatogram identified by the peak identification part 20.

The unidentified peak list display part 26 is configured to display the unidentified peak list created by the unidentified peak list creation part 24 on the display device 6. The unidentified peak list can be displayed together with the standard chromatogram and the analysis target chromatogram as shown in FIG. 2.

As described above, in the analytical data analysis system 2 of the present embodiment, the standard chromatogram and the analysis target chromatogram are displayed on the display device 6 in a state of being arranged side by side so as to be able to be visually compared with each other, and a peak expression position of the non-composition substance is described at least on the standard chromatogram. Accordingly, manual identification work is facilitated not only for the composition substance but also for the non-composition substance. Furthermore, since the unidentified peak list is also displayed on the display device 6, the user can easily recognize an unidentified peak.

An embodiment of an analytical data analysis system according to the present invention identifies composition substances contained in the sample to be analyzed and non-composition substances that are not the composition substance contained in the sample to be analyzed by comparing a standard chromatogram and an analysis target chromatogram. The standard chromatogram is a chromatogram created based on analytical data acquired by a chromatograph for a standard sample of a sample composed of specific composition substances. The analysis target chromatogram is a chromatogram created based on analytical data acquired by a chromatograph for a sample to be analyzed. The analytical data analysis system includes a display device for displaying information, a non-composition substance information holding part holding identification information and information on a peak expression position on a chromatogram of substances that may exist as the non-composition substance, a chromatogram synthesis part configured to synthesize the information held in the non-composition substance information holding part with the standard chromatogram in order to describe identification information and the peak expression position of the substances that may exist as the non-composition substance on the standard chromatogram in which the composition substances of the standard sample are described, and a chromatogram display part configured to display the analysis target chromatogram together with the standard chromatogram synthesized by the chromatogram synthesis part on the display device.

In the first aspect of the embodiment of the analytical data analysis system according to the present invention, the chromatogram synthesis part is configured to synthesize the information held in the non-composition substance information holding part with the analysis target chromatogram, so that the identification information and the peak expression positions of the substances that may exist as the non-composition substance are described on the analysis target chromatogram. By such an embodiment, the peak expression positions of the non-composition substance are described on the analysis target chromatogram, and the non-composition substances contained in the sample to be analyzed can be easily identified.

In the second aspect of the embodiment of the analytical data analysis system according to the present invention, the chromatogram display part is configured to display the standard chromatogram and the analysis target chromatogram arranged side by side on the display device in a state where time axes of the chromatograms are aligned with each other. Such an aspect facilitates visual comparison between the standard chromatogram and the analysis target chromatogram, and the efficiency of the identification work of the substance contained in the sample to be analyzed is improved.

In a third aspect of the embodiment of the analytical data analysis system according to the present invention, the chromatogram synthesis part is configured to synthesize the standard chromatogram so that the composition substances of the standard sample and the substances that may exist as the non-composition substance are described in a state that the substances are visually discriminated. By such an aspect, the expression positions of the composition substances and the non-composition substances can be easily visually grasped, and the efficiency of the identification work of the substance contained in the sample to be analyzed is improved.

A fourth aspect of the embodiment of the analytical data analysis system according to the present invention includes a peak identification part configured to identify individual peaks expressed on the analysis target chromatogram, an identification part configured to identify, using a substance described on the standard chromatogram synthesized by the chromatogram synthesis part, substances corresponding to the individual peaks identified by the peak identification part based on designation of a substance by the user or automatic determination using a predetermined condition, an unidentified peak list creation part configured to create a list of unidentified peaks not identified by the identification part among peaks identified by the peak identification part, and an unidentified peak list display part configured to display the unidentified peak list created by the unidentified peak list creation part on the display device. By such an aspect, the user can easily recognize unidentified peaks.

DESCRIPTION OF REFERENCE SIGNS

2 Analytical data analysis system
4 Arithmetic processing part
6 Display device
8 Analysis device
10 Standard sample data holding part
12 Non-composition substance information holding part
14 Chromatogram creation part
16 Chromatogram synthesis part
18 Chromatogram display part
20 Peak identification part
22 Identification part
24 Unidentified peak list creation part
26 Unidentified peak list display part

What is claimed is:

1. An analytical data analysis system for identifying composition substances contained in a sample to be analyzed and non-composition substances by comparing a standard chromatogram and an analysis target chromatogram, wherein the standard chromatogram is a chromatogram created based on analytical data acquired by a chromatograph for a standard sample of a sample composed of specific composition substances, the analysis target chromatogram is a chromatogram created based on analytical data acquired by a chromatograph for a sample to be analyzed, and the non-composition substances are substances which are not contained in the standard sample or are contained in the standard sample a negligibly small amount, the analytical data analysis system comprising:

a processor;

a display for displaying information; and a data storage configured to hold a first data source including a standard sample data, a second data source including a composition substance information, and a third data source including a non-composition substance information;

the composition substance information including identification information of the composition substances and information on peak expression positions on the composition substances;

the non-composition substance information including identification information of the non-composition substances and information on peak expression positions on the non-composition substances;

the processor is configured to synthesize the non-composition substance information with the standard chromatogram in order to describe the identification information and the peak expression positions of the non-composition substances on the standard chromatogram in which the composition substances of the standard sample are described; and/or the processor is configured to synthesize the non-composition substance information with the analysis target chromatogram, so that the identification information and the peak expression positions of the non-composition substances are described on the analysis target chromatogram, and the processor is configured to display the analysis target chromatogram together with the standard chromatogram on the display.

2. The analytical data analysis system according to claim 1, wherein the processor part is configured to display the standard chromatogram and the analysis target chromatogram arranged separately with two discrete display portions on the display in a state where time axes of the chromatograms are aligned with each other.

3. The analytical data analysis system according to claim 1, wherein
the processor is configured to synthesize the standard chromatogram so that the composition substances of the standard sample and the non-composition substances are described in a state that the substances are visually discriminated.

4. The analytical data analysis system according to claim 1, wherein the processor is configured to synthesize the non-composition substance information with the standard chromatogram in order to describe the identification information and the peak expression positions of the non-composition substances on the standard chromatogram in which the composition substances of the standard sample are described,
the processor is further configured to:
identify individual peaks expressed on the analysis target chromatogram;
identify, using a substance described on the synthesized standard chromatogram, substances corresponding to the identified individual peaks based on designation of a substance by the user or automatic determination using a predetermined condition; and
create a list of unidentified peaks not identified by the identification part among peaks identified by the peak identification part; and
display the unidentified peak list on the display.

* * * * *